US008734617B2

(12) United States Patent
Pape et al.

(10) Patent No.: US 8,734,617 B2
(45) Date of Patent: May 27, 2014

(54) PROCESS FOR PREPARING N,N-DIMETHYLAMINOETHOXYETHANOL

(75) Inventors: Frank-Friedrich Pape, Kleinniedesheim (DE); Alfred Krause, Sepyer (DE); Johann-Peter Melder, Böhl-Iggelheim (DE); Bernd Stein, Alsbach-Hähnlein (DE); Joachim-Thierry Anders, Gönnheim (DE); Frank Haese, Dietzenbach (DE)

(73) Assignee: BASF SE (DE)

( * ) Notice: Subject to any disclaimer, the term of this patent is extended or adjusted under 35 U.S.C. 154(b) by 311 days.

(21) Appl. No.: 13/421,249

(22) Filed: Mar. 15, 2012

(65) Prior Publication Data

US 2012/0264979 A1 Oct. 18, 2012

Related U.S. Application Data

(63) Continuation of application No. 12/293,699, filed as application No. PCT/EP2007/052629 on Mar. 20, 2007, now abandoned.

(30) Foreign Application Priority Data

Mar. 20, 2006 (EP) .................................... 06111382
Jul. 6, 2006 (EP) .................................... 06116712

(51) Int. Cl.
*B01D 3/34* (2006.01)
(52) U.S. Cl.
USPC ............................................. 203/38; 203/46
(58) Field of Classification Search
USPC .................................................... 203/38, 46
See application file for complete search history.

(56) References Cited

U.S. PATENT DOCUMENTS

| 3,131,132 A | 4/1964 | Moss et al. |
| 3,853,818 A | 12/1974 | Bechara et al. |
| 4,049,931 A | 9/1977 | Sandner et al. |
| 4,239,855 A | 12/1980 | Zimmerman |
| 4,379,024 A * | 4/1983 | Gardner ............................ 203/6 |
| 4,847,418 A | 7/1989 | Gibson et al. |
| 4,922,023 A | 5/1990 | Fischer et al. |
| 5,663,444 A | 9/1997 | Melder et al. |
| 6,521,707 B2 | 2/2003 | Podszun et al. |

FOREIGN PATENT DOCUMENTS

| DE | 4414879 A1 | 11/1995 |
| EP | 0 004 015 A1 | 9/1979 |
| EP | 0300323 A2 | 1/1989 |
| EP | 1203780 A1 | 5/2002 |
| JP | 62-51646 A | 3/1987 |
| JP | 8-143520 A | 6/1996 |
| JP | 9-20735 A | 1/1997 |

OTHER PUBLICATIONS

Cannon, J.G. et al., "Open-Chain Analogs of Muscarine Derivatives," *Journal of Pharmaceutical Sciences*, (May 1973), pp. 830-831, vol. 62, No. 5.
Sales-Cruz, et al, "Short-Path Evaporation for Chemical Product Modelling, Analysis and Design", European Symposium on Computer Aided Process Engineering, Elsevier, 2005.

* cited by examiner

*Primary Examiner* — Robert A Hopkins
(74) *Attorney, Agent, or Firm* — Drinker Biddle & Reath LLP

(57) ABSTRACT

Processes comprising: (a) reacting dimethylamine and ethylene oxide to form a product mixture comprising N,N-dimethylethanolamine and N,N-dimethylaminoethoxyethanol; (b) distilling the product mixture to obtain a bottom fraction comprising N,N-dimethylaminoethoxyethanol; and (c) distilling the bottom fraction to separate at least a portion of the N,N-dimethylaminoethoxyethanol from the bottom fraction; and apparatus for carrying out said processes.

11 Claims, No Drawings

PROCESS FOR PREPARING N,N-DIMETHYLAMINOETHOXYETHANOL

CROSS-REFERENCE TO RELATED APPLICATIONS

This application is a continuation application of U.S. patent application Ser. No. 12/293,699, filed Sep. 19, 2008 now abandoned, which is a national stage application, under 35 U.S.C. §371, of PCT/EP2007/052629, filed Mar. 20, 2007, which claims benefit of European Application No. 06111382.5, filed Mar. 20, 2006, and European Application No. 06116712.8, filed Jul. 6, 2006.

BACKGROUND OF THE INVENTION

2-[2-(dimethylamino)ethoxy]ethanol (N,N-dimethylaminoethoxyethanol, DMAEE) is a commercially available compound (BASF Corporation, USA), which finds use, for example, as an intermediate in the synthesis of active pharmaceutical ingredients or a catalyst in polyurethane preparation.

DMAEE is prepared firstly by reacting diethylene glycol with dimethylamine over a catalyst (see, for example, EP-A 0 303 323, JP-A 62/051646, JP-A 08/143,520 and JP-A 09/020, 735), and secondly by reacting N,N-dimethylethanolamine with ethylene oxide (see, for example, J. G. Cannon et al., Journal of Pharmaceutical Sciences 62 (1973) 830 and U.S. Pat. No. 3,853,818).

Even though some of the processes mentioned are performed on the industrial scale, there is still a great deal of room for improvement, for example with regard to yields, selectivity, reaction times or simple workup.

BRIEF SUMMARY OF THE INVENTION

The invention relates to a process for preparing N,N-dimethylaminoethoxyethanol, to an apparatus for performing it and to the use of by-products of the preparation of N,N-dimethylaminoethanol in such a process. It is an object of the invention to provide a process for preparing DMAEE which has advantages over the known processes at least in some aspects.

It has now been found that DMAEE forms in industrially utilizable amounts in the industrial preparation of N,N-dimethylethanolamine and can be removed in a simple manner in the purification of the N,N-dimethylethanolamine.

The invention therefore provides a process for preparing N,N-dimethylaminoethoxyethanol (DMAEE), wherein
a) dimethylamine and ethylene oxide are reacted,
b) the resulting product mixture of N,N-dimethylethanolamine and DMAEE is separated by distillation to obtain a DMAEE-containing fraction as the bot-tom stream, and
c) DMAEE from the fraction obtained in (b) is removed by distillation.

The invention further provides for the use of the bottom stream of a distillation of the reaction mixture of dimethylamine and ethylene oxide for obtaining DMAEE. The invention likewise provides an apparatus for performing the above-described process, comprising (I) a reactor, preferably a tubular reactor, with inlets for dimethylamine and ethylene oxide and an outlet for the reaction product, (II) a distillation apparatus for enriching the DMAEE by distillatively removing N,N-dimethylethanolamine from the reaction mixture with an outlet for the DMAEE-containing bottom product at the bottom of the distillation apparatus and (III) an apparatus which is suitable for fractional distillation and has an inlet for the DMAEE-containing reaction mixture at the bottom or at the side and an outlet for the distilled DMAEE in the top region of the apparatus.

The process according to the invention can provide DMAEE in a simple manner and without complicated synthesis with catalysts and complex product mixtures. It is also advantageous that, to obtain a color-stable pure material, hydrogenation over a noble metal catalyst is not necessary.

The reaction of ethylene oxide and dimethylamine to give mainly N,N-dimethylethanolamine and its process parameters are known, and it is used on the industrial scale for the preparation of N,N-dimethylethanolamine. Details of this reaction step are described, for example, in DE-A 44 14 879.

The reaction mixture formed comprises generally from 1 to 6% by weight, prefer-ably from 2 to 3% by weight, of DMAEE.

The DMAEE formed is removed by distillation from the main component, N,N-dimethylethanolamine, advantageously with a column operated continuously or batchwise within a temperature range (bottom) of from 40° C. to 150° C., preferably from 40° C. to 90° C., and at a pressure of from 5 to 1050 mbar, preferably from 5 to 300 mbar, more preferably from 10 to 150 mbar.

DMAEE is enriched in the bottom stream of this column.

To obtain pure DMAEE, the collected bottom stream is therefore fractionally distilled in a subsequent step.

Suitable column types for this distillation are all known column types, for example columns with random packing, tray columns, columns with structured packing and dividing wall columns. Preference is given to columns with structured packing and dividing wall columns. In a further preferred embodiment of the process, DMAEE is distilled at relatively low pressures, for example in a thin-film evaporator, falling-film evaporator or short-path evaporator, or one of the latter apparatuses with attached column of any type, for example a column with structured packing.

The fractional distillation in a column is effected generally within a temperature range (bottom) of from 40 to 250° C., preferably from 135 to 235° C., in particular from 170 to 200° C. The distillation is generally performed under reduced pressure, preferably within a range of from 1 to 1000 mbar, preferably from 100 to 500 mbar, more preferably 400 mbar. The reflux ratio is generally from approx. 1.5:1 (reflux to withdrawal) to 5:1.

In the further preferred embodiment of the process in a thin-film evaporator, falling-film evaporator or short-path evaporator, the distillation is effected at distillation temperatures of from 40 to 150° C., preferably from 40 to 100° C., and under a pressure of from 0.001 to 1 mbar, preferably from 0.01 to 0.1 mbar.

It is known to the person skilled in the art that relatively low distillation temperatures are possible with very good vacuum and the product can be distilled more gently as a result. In this distillation, it was found that, surprisingly, the DMAEE product remains stable even under relatively severe distillation conditions (see table 1) and could be isolated with very good yields and purities.

The DMAEE obtained in this step generally has a purity of ≥98%, preferably ≥99%, and a APHA color number of <70, preferably <20 APHA (see table 1). The secondary components present are mainly small amounts of glycol, vinyloxyethanol and N,N-dimethylethanolamine, and slight discoloration, which is reestablished even after the distillation, is attributable essentially to traces of yl-nyloxyethanol.

In a preferred embodiment of the invention, vinyloxyethanol is therefore removed from DMAEE or destroyed by adding phosphorous acid, $H_3PO_3$.

In this case, either the DMAEE obtained in step c) can be subjected to a further distillation in which phosphorous acid is added, or the phosphorous acid is added actually in the course of the fractional distillation.

It is possible to use the phosphorous acid in crystalline form or as a mixture of phosphorous acid and water. Both crystalline material and aqueous solutions are commercially available (for example from Supresta or Honeywell).

Preference is given to the addition of a mixture of phosphorous acid and water, more preferably in a weight ratio of 1:10 to 10:1, in particular of 1:1. In general, from 0.01 to 10 parts by weight, preferably from 0.25 to 1 part by weight, of phosphorous acid per 25 parts by weight of the mixture to be distilled are used.

The above-described advantage that DMAEE remains stable even at relatively high temperatures in the distillation is utilized especially in this preferred embodiment of the process because phosphorous acid $H_3PO_3$ is particularly active for the destruction of vinyloxyethanol (VOE) at elevated temperature. This reaction proceeds particularly advantageously at from 150° C. to 200° C. Especially at from 180° C. to 190° C., relatively small amounts of $H_3PO_3$ are required. For this reason, a distillation at from 400 to 600 mbar is particularly advantageous, because a bottom temperature of from 175 to 200° C., preferably from 180 to 190° C., is then established in the distillation.

In both variants, the distillation mixture is heat-treated with full reflux at a temperature of from 175 to 200° C., preferably from 180 to 190° C., and a pressure of from 400 to 600 mbar, preferably about 500 mbar, preferably for from 1 to 3 h, in particular about 2 h.

When the vinyloxyethanol is removed or destroyed in a separate distillation, this is preferably performed by means of a tray column, column with random packing, column with structured packing or dividing wall column, more preferably a column with structured packing or a dividing wall column under the pressure and temperature conditions specified above.

Further secondary components can be removed by known methods familiar to those skilled in the art; for example, the main secondary component glycol can be removed, for example, as a high-boiling acetal by adding a suitable higher aldehyde.

The resulting DMAEE is suitable, for example, as an intermediate for the synthesis of active pharmaceutical ingredients or a catalyst in polyurethane preparation.

The invention is illustrated in detail by the examples without thereby restricting it.

EXAMPLE 1

Distillation of the Bottom Stream of a Column for Removing N,N-dimethylethanolamine The crude product of the industrial scale reaction of dimethylamine and ethylene oxide is subjected to a distillation to remove N,N-dimethylethanolamine.

The bottom residue of the column has the following composition in GC area %:

| | |
|---|---|
| Glycol: | 6% |
| Vinyloxyethanol: | 4% |
| N,N-dimethylethanolamine: | 16% |
| Dimethylaminoethoxyethanol: | 74% |

918 g of this residue were subjected to a distillation by means of a 1 m column with random packing (diameter: 60 mm, random packings: 3×3 mm). The result is shown in table 1.

TABLE 1

| | Distillation | | | | | | | |
|---|---|---|---|---|---|---|---|---|
| Fraction | Fr. 1 | Fr. 2 | Fr. 3 | Fr. 4 | Fr. 5 | Fr. 6 | Fr. 7 | Fr. 8 |
| Color number | 11 APHA | 7 APHA | 26.5 APHA | 25.5 APHA | 7 APHA | 5 APHA | 13 APHA | 68 APHA |
| Weight in g | 21 | 84 | 66 | 81 | 120 | 128 | 133 | 143 |
| Bottom T in ° C. | 135-142 | 170-178 | 178-182 | 182 | 182-183 | 183 | 174-176 | 196-235 |
| Distillation T in ° C. | 66-70 | 98-106 | 158-160 | 160 | 158-159 | 155-156 | 165-167 | 165-112 |
| Pressure in mbar | 125-123 | 415-424 | 436-426 | 426-422 | 421 | 420-418 | 308-312 | 312-35 |
| Reflux/efflux | 05:02 | 05:02 | 10:01 | 10:02 | 10:02 | 10:02 | 04:02 | 03:02 |
| Composition GC area % | | | | | | | | |
| Glycol | 0.00 | 0.00 | 29.53 | 38.85 | 31.92 | 0.37 | 0.00 | 0.00 |
| Vinyloxyethanol | 0.02 | 30.17 | 18.59 | 0.28 | 0.18 | 0.21 | 0.05 | 0.04 |
| Dimethylethanolamine | 99.98 | 69.83 | 6.61 | 0.17 | 0.11 | 0.15 | 0.06 | 0.08 |
| DMAEE | 0.00 | 0.00 | 45.27 | 60.7 | 67.79 | 99.27 | 99.89 | 99.88 |
| Total % | 100.00 | 100.00 | 100.00 | 100.00 | 100.00 | 100.00 | 100.00 | 100.00 |
| Residue | 94 g | | 29.26 | 49.13 | 81.07 | 124.99 | 131.87 | 141.70 |

The dimethylaminoethoxyethanol obtained in fractions 6 to 8 corresponded to an isolated yield of about 72%. The starting material was very dark in color. The distillation improved the color number significantly.

EXAMPLE 2

Distillation over $H_3PO_3$

From the distillation of example 1, fractions 6 and 7 were combined and 250 g thereof were mixed with a mixture of 2.5 g of distilled water and 2.5 g of phosphorous acid $H_3PO_3$. The homogeneous mixture was heat-treated at 185° C. for 2 hours and then distilled by means of a 20 cm column at 500 mbar and 182-184° C.

TABLE 2

| | Distillation over H₃PO₃ | |
|---|---|---|
| | (Fr. 6 + Fr. 7) | Distillate |
| Color number (APHA) | 19 | 0 |
| Composition GC area % | | |
| Glycol | 0.20 | 0.26 |
| Vinyloxyethanol | 0.13 | 0.00 |
| Dimethylethanolamine | 0.12 | 0.08 |
| DMAEE | 99.55 | 99.66 |
| Total % | 100.00 | 100.00 |

The treatment with phosphorous acid and subsequent distillation virtually quantitatively affords colorless N,N-dimethylaminoethoxyethanol (DMAEE) which, by GC, no longer comprises any vinyloxyethanol.

EXAMPLE 3

Combination of distillation and removal of vinyloxyethanol in a single step.

In a column with random packing (length: 1 m, diameter: 60 mm, 3×3 mm random packings, reflux divider, approx. 30 theoretical plates), 250 g of a crude material with the following composition were introduced into the still: 6.85% Glycol, 4.50% vinyloxyethanol, 15.20% dimethylethanolamine, 70.70% N,N-dimethylaminoethoxyethanol (DMAEE), 0.08% (dimethylaminoethyl) vinyl ether.

The 250 g of the crude material were mixed with a mixture of 10 g of distilled water and 10 g of phosphorous acid. The bottom temperature in the column was adjusted to 145° C. with full reflux, and heating to reflux was continued for 2 h. After these 2 hours, a sample was taken from the column bottoms and the following composition was found: 0.01% vinyloxyethanol, 0.1% methanol, 1.69% methyldioxalane, 2.50% glycol, 6.44% N,N-dimethylethanolamine (DMEOA), 1.78% N-ethyl-N-methylethanolamine and 74.30% N,N-dimethylaminoethoxyethanol (DMAEE).

Subsequently, fractional distillation was effected at column pressure 500 mbar, a ratio of reflux to efflux of approx. 5:1-2:1, bottom temperature 180° C. and distillation temperature 30-72° C., then 72-150° C. Approx. 25% first runnings were removed, which consisted especially of methyldioxalane, N-methylmorpholine, N,N-dimethylethanolamine (DMEOA) and glycol.

Subsequently, the vacuum was lowered to 100 mbar, and distillation was continued at a bottom temperature of 138° C. rising up to 200-250° C., a constant distillation temperature of 130° C. and a ratio of reflux to efflux of 4:5. The pure product was obtained in a purity of 77-99%; the vinyloxyethanol (VOE) content in all pure fractions was significantly less than 0.1%. 145 g of the N,N-dimethylaminoethoxyethanol (DMAEE) product of value were obtained; this corresponds to approx. 82% yield based on the DMAEE present in the crude material (176 g) and 58% yield based on the total mass of the crude material used at the outset (250 g).

The invention claimed is:

1. A process comprising: (a) reacting dimethylamine and ethylene oxide to form a product mixture comprising N,N-dimethylethanolamine and N,N-dimethylaminoethoxyethanol; (b) distilling the product mixture to obtain a bottom fraction comprising N,N-dimethylaminoethoxyethanol; and (c) distilling the bottom fraction to separate at least a portion of the N,N-dimethylaminoethoxyethanol from the bottom fraction.

2. The process according to claim 1, wherein distilling the product mixture is carried out at a bottom temperature of 40 to 150° C. and at a pressure of 5 to 1050 bar.

3. The process according to claim 1, wherein distilling the bottom fraction comprises fractional distillation carried out in a column.

4. The process according to claim 3, wherein the fractional distillation is carried out at a bottom temperature of 40 to 280° C. and a pressure of 1 to 1000 mbar.

5. The process according to claim 1, wherein distilling the bottom fraction comprises fractional distillation carried out in one or more devices selected from the group consisting of a thin-film evaporator, a falling-film evaporator, and a short-path evaporator, optionally in conjunction with an attached column.

6. The process according to claim 5, wherein the distillation is carried out at a distillation temperature of 40 to 150° C. and at a pressure of 0.001 to 1 mbar.

7. The process according to claim 1, wherein phosphorous acid is added to the distillation of the bottom fraction.

8. The process according to claim 1, further comprising distilling the N,N-dimethylaminoethoxyethanol obtained from the bottom fraction over phosphorous acid.

9. An apparatus for carrying out the process according to claim 1, the apparatus comprising: (I) a tubular reactor an inlet for the dimethylamine, an inlet for the ethylene oxide, and an outlet for the product mixture; (II) a distillation apparatus for enriching the N,N-dimethylaminoethoxyethanol in the product mixture by distillatively removing N,N-dimethylethanolamine from the product mixture with an outlet for the bottom fraction at a bottom of the distillation apparatus; and (III) an apparatus which is suitable for fractional distillation and which has an inlet for the bottom fraction at a bottom or at a side of the apparatus, and an outlet at a top region of the apparatus for the distilled portion of N,N-dimethylethanolamine.

10. The apparatus according to claim 9, wherein the apparatus (III) suitable for fractional distillation comprises a column.

11. The apparatus according to claim 9, wherein the apparatus (III) suitable for fractional distillation comprises one or more devices selected from the group consisting of a thin-film evaporator, a falling-film evaporator, and a short-path evaporator, optionally in conjunction with an attached column.

* * * * *